United States Patent
Breitenstein et al.

(10) Patent No.: US 8,241,036 B2
(45) Date of Patent: Aug. 14, 2012

(54) IMPLANT WITH A CERAMIC COATING, AND METHOD FOR CERAMIC COATING OF AN IMPLANT

(75) Inventors: Michael Breitenstein, Wenslingen (CH); Marco Wieland, Basel (CH)

(73) Assignee: Straumann Holding AG, Basel (CH)

( * ) Notice: Subject to any disclaimer, the term of this patent is extended or adjusted under 35 U.S.C. 154(b) by 818 days.

(21) Appl. No.: 10/971,126

(22) Filed: Oct. 25, 2004

(65) Prior Publication Data

US 2005/0113834 A1    May 26, 2005

(30) Foreign Application Priority Data

Oct. 27, 2003   (EP) ................................. 03405769

(51) Int. Cl.
*A61C 8/00*    (2006.01)
(52) U.S. Cl. ........................................... 433/173
(58) Field of Classification Search .............. 623/16; 433/172–176, 201.1
See application file for complete search history.

(56) References Cited

U.S. PATENT DOCUMENTS

| | | | | |
|---|---|---|---|---|
| 4,746,532 A * | 5/1988 | Suzuki et al. | ................. | 428/336 |
| 4,801,300 A | 1/1989 | Kurze et al. | | |
| 4,846,837 A * | 7/1989 | Kurze et al. | ................. | 623/23.6 |
| 5,125,971 A * | 6/1992 | Nonami et al. | ................. | 106/35 |
| 5,199,873 A * | 4/1993 | Schulte et al. | ................. | 433/174 |
| 5,478,237 A * | 12/1995 | Ishizawa | .................... | 433/201.1 |
| 5,571,017 A | 11/1996 | Niznick | | |
| 5,613,849 A * | 3/1997 | Tanaka et al. | ..................... | 433/8 |
| 5,620,323 A * | 4/1997 | Bressman et al. | ............ | 433/174 |
| 5,711,669 A * | 1/1998 | Hurson | .......................... | 433/174 |
| 5,763,092 A * | 6/1998 | Lee et al. | ...................... | 428/469 |
| 5,833,463 A * | 11/1998 | Hurson | .......................... | 433/173 |
| 5,863,201 A * | 1/1999 | Lazzara et al. | ............. | 433/201.1 |
| 5,879,161 A * | 3/1999 | Lazzara | ........................ | 433/173 |
| 5,964,767 A * | 10/1999 | Tapia et al. | ..................... | 606/323 |
| 6,193,516 B1 * | 2/2001 | Story | ............................. | 433/173 |
| 6,217,331 B1 * | 4/2001 | Rogers et al. | ................. | 433/173 |
| 6,287,116 B2 * | 9/2001 | Lazzara | ........................ | 433/173 |
| 6,379,153 B1 * | 4/2002 | Schroering | ................... | 433/173 |
| 6,558,428 B2 * | 5/2003 | Park | ............................. | 623/23.59 |
| 6,758,672 B2 * | 7/2004 | Porter et al. | .................. | 433/173 |
| 2004/0121290 A1* | 6/2004 | Minevski et al. | .......... | 433/201.1 |

(Continued)

FOREIGN PATENT DOCUMENTS

EP    0534078    3/1993

(Continued)

OTHER PUBLICATIONS

Search Report from European Patent Office in corresponding application EP 03405769, dated May 6, 2004.

(Continued)

*Primary Examiner* — Eduardo C Robert
*Assistant Examiner* — Ann Schillinger
(74) *Attorney, Agent, or Firm* — Rissman Hendricks & Oliverio LLP

(57) ABSTRACT

Implant (1) with a base body having at least one bone contact surface (K) and at least one soft tissue contact surface (W), characterized in that the soft tissue contact surface (W) and/or a transition area (U) from bone contact surface (K) to soft tissue contact surface (W) have/has at least partially a ceramic coating (2), and in that the bone contact surface (K) has areas not provided with a ceramic coating (2).

34 Claims, 2 Drawing Sheets

U.S. PATENT DOCUMENTS

2005/0106534 A1 * 5/2005 Gahlert .................. 433/173

FOREIGN PATENT DOCUMENTS

| EP | 0606566 A1 | 7/1994 |
|---|---|---|
| EP | 0534978 | 3/1999 |
| FR | 2788963 | 8/2000 |
| JP | 05-305132 A | 11/1993 |
| JP | 06-133992 A | 5/1994 |
| JP | 06-225891 A | 8/1994 |
| JP | 08-117250 A | 5/1996 |

OTHER PUBLICATIONS

English translation of Feb. 10, 2010 Decision of Rejection in corresponding JP 2004-312180.

* cited by examiner

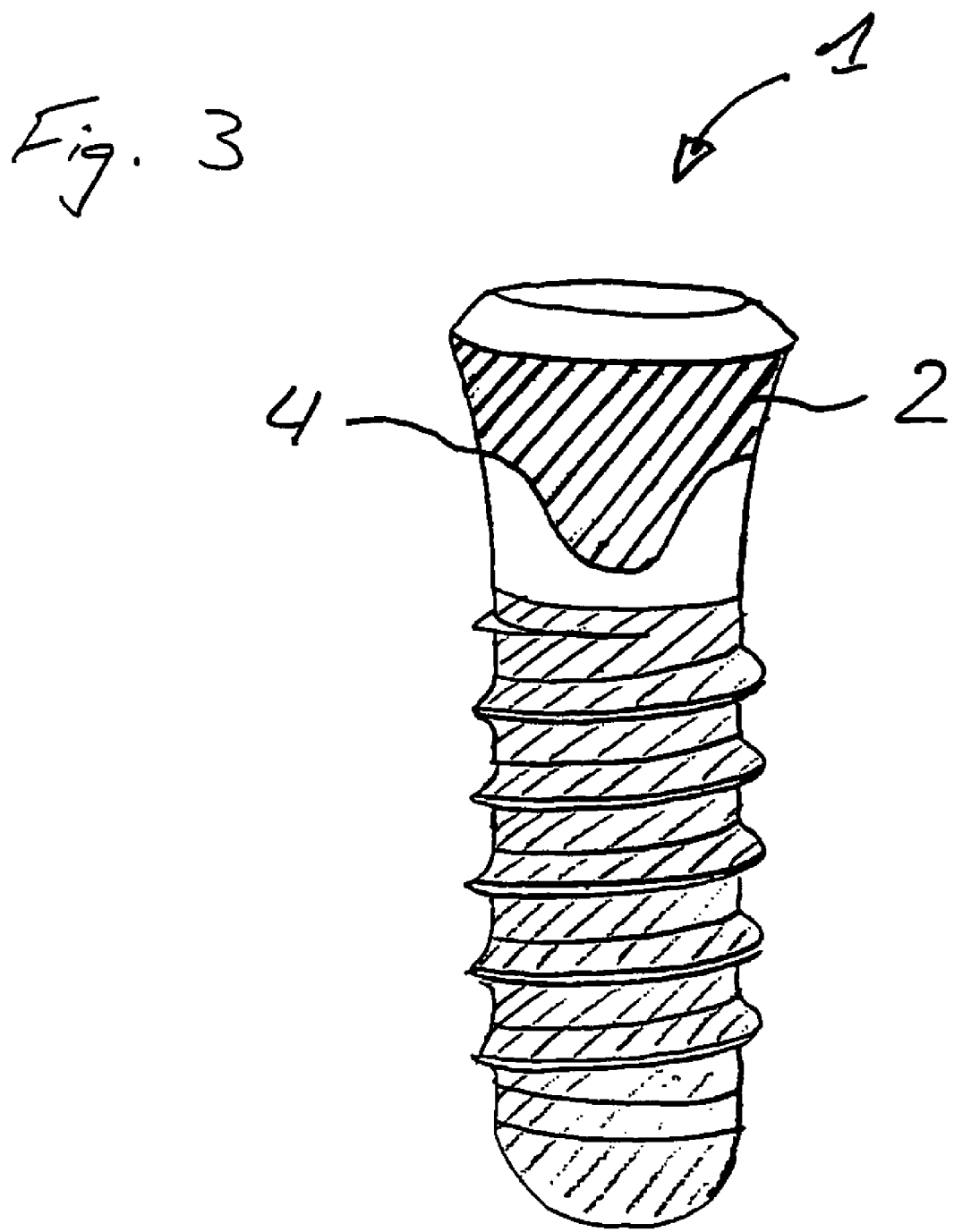

IMPLANT WITH A CERAMIC COATING, AND METHOD FOR CERAMIC COATING OF AN IMPLANT

FIELD OF THE INVENTION

The invention relates to implants with a ceramic coating, and to a method for ceramic coating of an implant.

BACKGROUND

In the field of dental implantology in particular, implants have in practice proven useful in which the bone contact surface is made of metals, in particular of titanium or of titanium alloys. In the hydroxylated and hydrophilic state in particular, such materials can provide excellent osseointegration (see, for example, WO 00/44305).

In the area of the soft tissue, by contrast, such materials are associated with disadvantages. On the one hand, the darkish metal implant shows through the soft tissue, as a result of which the visual impression created by such treatment may be marred. In addition, reports have described how it is possible with other materials, for example ceramics, to achieve an improved tissue reaction in the soft tissue area (see German utility model DE-U1-298 20 971, for example).

It is thus known, from a large number of documents, to equip a metal implant with a ceramic sleeve arranged in the area of the soft tissue contact surface (see, for example, documents DE-U1-298 20 971, U.S. Pat. No. 5,152,687, FR-B3-2 788 963, GB-A-2 139 095). Ceramic sleeves of this kind are, for example, sintered or adhesively bonded onto the implant. As a result, however, a number of problems arise which have not as yet been resolved. On the one hand, using a ceramic sleeve as a separate structural part almost unavoidably results in a micro-gap, which in particular can cause bacterial contamination.

By contrast, when such a sleeve is fitted by sintering, such high temperatures generally have to be used that the metallic base body of the implant at least partially oxidizes. However, this has a disadvantageous effect on osseointegration. Moreover, different coefficients of thermal expansion of the materials involved can result, particularly during cooling, in the development of microstresses, and these can lead to hairline fractures and cracks.

It is known, for example from document EP-B1-0 211 676, to provide titanium implants with a ceramic coating of the entire implant body. It has likewise been proposed to provide the bone contact surface of an implant with a biocompatible coating, for example of hydroxyapatite or calcium phosphate (e.g. U.S. Pat. No. 5,478,237). However, by doing so, the proven advantageous properties of titanium in respect of osseointegration are no longer available.

Many methods of coating a substrate are known:

Coatings can be applied by means of CVD or PVD (chemical vapour deposition or physical vapour deposition). A disadvantage of these methods is that adhesion to the surface is generally not optimal and the coating may be brittle. Moreover, the colour of a coating obtainable in this way cannot generally be influenced to the desired extent by its thickness.

Coatings with silicate glass and with silicate-glass-modified ceramics are also known, for example from document WO 01/74730. A disadvantage of these is, once again, the possibility of microstresses occurring as a result of the firing process at high temperatures and the at least partial oxidation of the titanium surface.

It is also known to coat metals such as aluminium, titanium or tantalum by means of anodic oxidation under spark discharge. Document DE-C1-43 03 575 describes the production of implants coated with apatite. Document DD-A1-246 028 describes a metal implant which, in the bone contact area, is coated with a calcium phosphate ceramic. Here again, however, the proven advantageous properties of titanium in particular with respect to osseointegration are no longer available.

SUMMARY OF THE INVENTION

According to various embodiments of the invention the disadvantages of the known implants are avoided and in particular, an implant is provided having the proven and advantageous properties that known implants, in particular those of titanium and titanium alloys, have in respect of osseointegration. Moreover, various embodiments of the invention make available an implant which has improved compatibility and avoids metal showing through in the soft tissue area. Such an implant should also be able to be produced cost-effectively and using established methods.

According to various embodiments of the invention, there is provided an implant and a method for ceramic coating of an implant.

In one embodiment according to the invention, an implant, in particular a dental implant, has a base body having at least one bone contact surface and at least one soft tissue contact surface, and the soft tissue contact surface and/or a transition area from bone contact surface to soft tissue contact surface have/has at least partially a ceramic coating. Preferably, the entire bone contact surface is not provided with a ceramic coating. However, the bone contact surface has at least some areas which are not provided with a ceramic coating. Here, and in the rest of the text, the transition area from bone contact surface to soft tissue contact surface is intended to mean those surfaces of the implant which, in the implanted state, may possibly come into contact both with surrounding soft tissue and also with the bone. With such an implant, the known advantageous and proven osseointegration properties of, for example, titanium are still available in the area of the bone contact surface. Titanium or a titanium alloy is a preferred material of the base body of an implant according to the invention, but the invention is not limited thereto. At least the base body of the implant can be made of any tissue-compatible material, in particular of a tissue-compatible metal or an alloy of such metal, for example, besides titanium, also tantalum, zirconium and hafnium, and also alloys of these metals, in particular with in each case added amounts of niobium and/or tantalum and/or hafnium. In the area of the soft tissue contact surface, the ceramic coating affords improved tissue compatibility and an improved appearance. The for the most part white or whitish gray ceramic coating does not show through the soft tissue, or does so only negligibly; moreover, the ceramic coating can easily be adapted in colour by means of suitable admixtures, which are known to the person skilled in the art, so that it is also readily possible to achieve colour shades (for example the colour of the gums, pink, etc.). Here, and in the rest of the text below, ceramic coatings are understood to mean fine, compact, speciality ceramic materials, in particular oxide ceramics.

In a preferred embodiment, the bone contact surface not provided with a ceramic coating is treated in such a way that an improved osseointegration is obtained. Such treatments are described, for example, in WO 00/44305 and WO 02/07792, the content of which is incorporated herein by reference. Preferred embodiments of such a surface treatment particularly concern treatments which result in a roughened surface in a hydroxylated and hydrophilic state. In this case, maximum peak-to-valley heights $R_{max}$ of 0.1 µm to 50 µm according to DIN 4768 are preferred (profile height within the measurement section) which can be achieved by, inter alia, mechanical treatment (for example sandblasting, shotpeening, etc.) and/or by chemical treatment (for example etching) or by electrochemical processes.

In a particularly preferred embodiment of the invention, the ceramic coating is applied by a method of anodic oxidation, in particular under spark discharge. A method for anodic oxidation under spark discharge (ANOF) is described, inter alia, in documents DE-C1-43 03 575 and DD-A1-246 028 and also in Z. Klin. Med. 41 (1986), volume 3, pages 219-222, the content of these documents is incorporated herein by reference. This involves a method of layer formation in which an oxide layer is melted under plasma conditions. Such an oxide layer is preferably a substantially same-type oxide layer (for example base body of the implant made of titanium: titanium oxide coating, etc.), but the invention is not intended to be limited to such embodiments. By means of anodic oxidation under spark discharge, it is possible to achieve especially high adhesive strength of the applied coating of >8 MPa, so that coatings obtainable in this way are preferable, in terms of stability, to coatings obtainable by other means. In addition, it is not necessary to perform a final firing of the coating, as a result of which the bone contact surface made of titanium or of titanium alloy would be affected and would in particular be at least partially oxidized. In order to improve the adhesive strength of the ceramic coating, that area of the base body of the implant intended to be coated is first of all roughened, for example by etching.

The ceramic coating particularly preferably contains a titanium oxide ceramic and/or zirconium oxide ceramic and/or an aluminium oxide ceramic. Such coatings are used particularly advantageously as same-type coatings, for example the base body of an implant of titanium is preferably provided with a titanium oxide ceramic. However, it is also possible to use coatings of other types and also mixtures, for example in order to achieve particular shades of colour or defined peak-to-valley heights.

According to a further particularly preferred embodiment, the thickness of the ceramic coating is 1 nm to 1 mm, preferably 200 nm to 100 µm. The thickness of the ceramic coating is particularly chosen such that the metal material of the base body of the implant does not show through the soft tissue.

In a further embodiment of the invention, the chemical composition and/or a physical property of the ceramic coating varies, in particular continuously, along the thickness of the layer. In particular, it is possible, for example, by admixing material during deposition of the coating, especially by anodic oxidation under spark discharge, to vary the colour along the thickness of the layer and obtain a defined depth of colour. For specific application purposes, however, it is also possible to gradually admix, along the thickness of the ceramic coating, a component which for example further improves the soft tissue compatibility, for example calcium, phosphates, collagen, fibrin, amino acids, active enamel substances, such as EMDOGAIN®, etc. Moreover, it is conceivable to vary a physical property of the ceramic coating along the thickness of the coating, in particular the density and/or the pore size, in which case the pore size is preferably chosen as small as possible on account of the potential attachment of bacteria and other contaminants. In this way, an influence can be exerted selectively on the nature of the surface, by which means the interaction with surrounding tissue can be influenced.

According to a further embodiment of the invention, the ceramic coating has a peak-to-valley height $R_{max}$, according to DIN 4768, of 100 nm to 100 µm, preferably of 100 nm to 50 µm, particularly preferably of 100 nm to 5 µm. Such a peak-to-valley height of the surface can be obtained both during application, in particular by anodic oxidation by means of spark discharge, and also by subsequent treatment to remove material, in particular mechanical treatment. The peak-to-valley height is in this case chosen such that an advantageous interaction with surrounding tissue is obtained, but without creating a hygienically problematic environment inducive to bacteria, for example caused by too coarse a structuring, in particular a coarse and open porosity. Of course, additional treatments of the ceramic coating, for example etching or sandblasting, are also possible after the application, in particular in order to modify the quality of the surface.

According to further advantageous embodiments of the invention, a transition area from bone contact surface to soft tissue contact surface can in particular be formed in various ways.

Thus, it is possible and advantageous that the thickness of the ceramic coating decreases, in particular continuously, towards the bone contact surface. It is of course possible that the thickness of the layer decreases, in particular continuously, along its entire extent or also only in a transition area from bone contact surface to soft tissue contact surface. The variation in thickness can be effected during the application or deposition of the ceramic coating and also subsequently by material-removing treatment, in particular mechanical treatment.

In a further advantageous embodiment, the ceramic coating extends as far as a projection in particular in a transition area from bone contact surface to soft tissue contact surface, which projection is compensated by the ceramic coating. In this case, it is not necessary to reduce the thickness of the ceramic coating in a transition area from bone contact surface to soft tissue contact surface so as to avoid protruding end edges, and for this reason the production of such an implant is considerably simplified.

According to a particularly preferred embodiment of an implant according to the invention, the edge of the ceramic coating facing toward the bone contact surface and extending along the circumference of the implant is formed in a curved shape, with at least one rise, preferably two such rises, and one dip, preferably two such dips, so that the natural shape of the bone is simulated by this edge. In this way it can be ensured that, ideally, all the soft tissue contact surfaces are provided with the ceramic coating, and uncoated surfaces not in contact with the bone are not present in particular in a transition area from bone contact surface to soft tissue contact surface. With such a configuration of the edge of the ceramic coating, it is possible to effectively avoid the colour of the base body of the implant showing through the soft tissue in the implanted state. The configuration of the edge can in this case be made universal to match most bone shapes but can also be made individual, that is to say for each individual implant. In particular, it is possible, by means of CAD/CAM, to exactly register the surface of the implant to be coated via the bone shape of the patient and to provide the implant with the ceramic coating accordingly. It is also possible, by removal of material, to adapt a ceramic coating, which has been applied in excess, to the individual conditions of the bone.

The invention moreover relates to a method for in particular ceramic coating of an implant, in which method a ceramic coating is applied only to the soft tissue contact surface and/or to a transition area between bone contact surface and soft tissue contact surface of an osteophilic implant. A method of anodic oxidation, in particular under spark discharge, is preferably employed for this purpose.

In a preferred embodiment, areas of the implant are at least temporarily covered over so that they are not accessible to a ceramic coating. For this purpose, elastomeric coverings are preferably used, for example the fluoroelastomer Viton® from DuPont Dow Elastomers. It is in this way possible, by simple means, to perform precision coating of only the desired area of the base body of the implant.

According to a further preferred embodiment, the surface of the ceramic coating is at least partially roughened by physical and/or chemical processes. Such a roughening of the surface can in particular be effected by mechanical treatment (for example sandblasting, shotpeening, etc.) and/or by chemical treatment (for example etching) or also electro-chemical processes. Such roughening, carried out subsequently, can be additional to the roughening which has already been obtained, for example during coating by means of anodic oxidation under spark discharge, and which is controllable to a certain extent.

BRIEF DESCRIPTION OF THE FIGURES

The invention is explained below on the basis of figures and illustrative embodiments, without in any way limiting the invention to the embodiments shown. The drawing shows the following:

FIG. 3: a ceramic coating imitating the natural shape of the bone.

DETAILED DESCRIPTION

Figure 1:
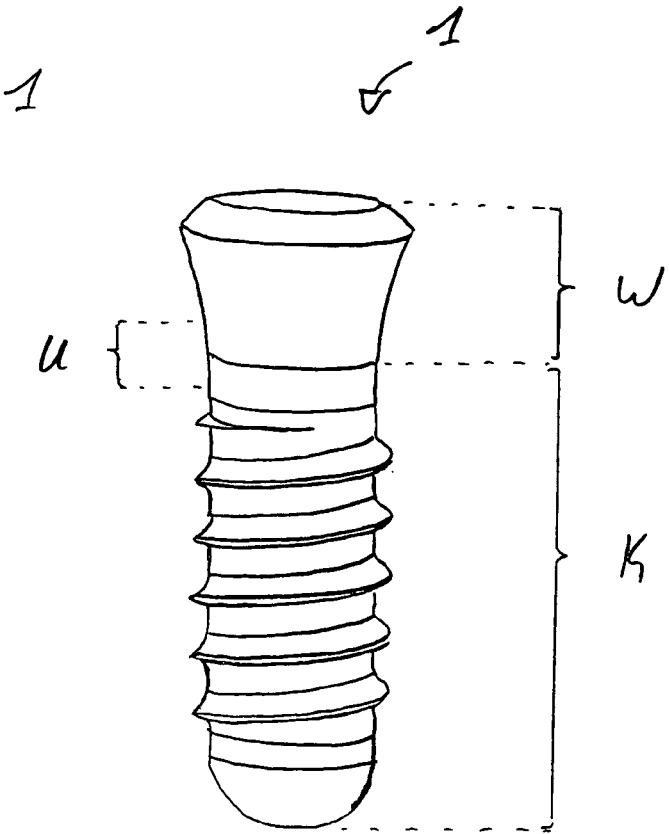
FIG. 1: different surfaces of an implant.

FIG. 1 shows the different areas of an implant 1. Such an implant 1 is preferably made of a tissue-compatible metal or of an alloy of such a metal, in particular of titanium or of a titanium alloy. An implant 1 is subdivided into at least one bone contact surface K and one soft tissue contact surface W. In the boundary area of these surfaces, there is a transition area U from bone contact surface K to soft tissue contact surface W, which transition area U is assigned to both aforementioned surfaces. The question of whether this area, in the implanted state, is located in the bone or in the soft tissue depends on a large number of factors, for example the depth to which the implant is screwed, the tissue reaction, etc. In the area of the bone contact surface K and of the transition area U, the surface can be treated in such a way as to improve the osseointegration properties of the implant 1. In the case of implants 1 made of titanium, a roughened, hydroxylated and hydrophilic surface is preferred. Of course, the invention is not limited to the implant configuration illustrated, and in particular not limited to the interface illustrated for the securing of an attachment part; a ceramic coating 2 in the sense of the present invention is expedient and realizable with any implant 1, as long as a defined area of the implant 1 is to be arranged in the soft tissue, that is to say as long as the implant 1 has a soft tissue contact surface.

Figure 2:
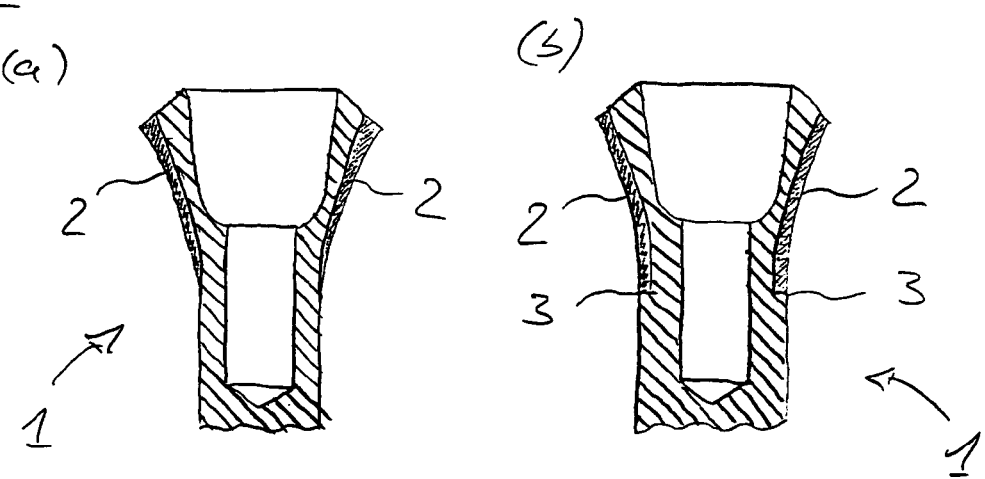
FIGS. 2*a,b*: configurations of the ceramic coating of an implant.

FIG. 2 shows an implant 1 according to FIG. 1 with a ceramic coating 2. The ceramic coating 2 is arranged in the area of the soft tissue contact surface W and of the transition area U from bone contact surface K to soft tissue contact surface W. FIG. 2*a* shows an illustrative embodiment in which the thickness of the ceramic coating 2 decreases continuously towards the bone contact surface K. According to the invention, however, it is of course also possible, for example, that the thickness of the ceramic layer decreases, in particular continuously, only in an area contiguous to the bone contact surface, in particular in the transition area U. Such a variation in the thickness of the layer can already be realized when applying the ceramic coating, although it can also be realized subsequently, in particular by mechanical treatment. FIG. 2*b* shows an embodiment in which the ceramic coating 2 reaches as far as a projection 3 of the implant, in particular in a transition area U of the implant, the projection 3 being compensated by the ceramic coating 2. Such a configuration of an implant 1 according to the invention ensures particularly simple production, since the thickness of the ceramic coating 2 does not have to be adapted, neither during production nor subsequently. In the case where a ceramic coating 2 is applied by a method of anodic oxidation under spark discharge, the thickness of the coating 2 can be influenced, by suitable choice of the duration of deposition, in such a way as to compensate exactly for the projection 3. The bevelled top end area of the implant 1, as shown in FIGS. 2*a* and 2*b*, is not provided with a ceramic coating 2 in this illustrative embodiment; this area forms the interface to an attachment element (not shown in detail) and is therefore advantageously left free from the ceramic coating 2.

FIG. 3 shows a particularly preferred embodiment of an implant 1 provided according to the invention with a ceramic coating 2. In this case, the edge 4 of the ceramic coating 2 is formed along the circumference of the implant 1 in a curved shape, with at least one rise and one dip, so that, in the implanted state, the natural shape of the bone is simulated by this edge 4. In this way it is possible to ensure that, ideally, all the soft tissue contact surfaces W are provided with the ceramic coating 2, and uncoated surfaces not in contact with the bone are not present, in particular, in a transition area U from bone contact surface K to soft tissue contact surface W. Particularly in the area of the bone contact surface K, a surface treatment can once again be provided for improved osseointegration, in particular a roughened, hydroxylated or hydrophilic surface. In this case, such surface treatment does not necessarily have to reach as far as the ceramic coating 2.

The invention claimed is:

1. A dental implant comprising:
    an integral base body of the dental implant having a bone contact surface,
    a soft tissue contact surface of the dental implant, and
    a transition area of the dental implant from the bone contact surface to the soft tissue contact surface,
    wherein the base body comprises an osseointegration-compatible metal or of an alloy of such a metal,
    wherein the soft tissue contact surface and at least a portion of the transition area adjacent the soft tissue contact surface comprises a ceramic coating applied by an anodic oxidation under spark discharge and contains at least one of a titanium oxide ceramic, zirconium oxide ceramic, and aluminum oxide ceramic,
    wherein the bone contact surface is not provided with the ceramic coating to preserve the osseointegration-compatible properties of the metal or metal alloy base body, and
    wherein a thickness of the ceramic coating in the transition area decreases towards the bone contact surface.

2. The dental implant according to claim 1, wherein the ceramic coating is a same-type coating comprising an oxide ceramic of the same metal or metal alloy as the oxide ceramic comprising the base body.

3. The dental implant according to claim 1, wherein the base body is made at least partially of titanium or of a titanium alloy.

4. The dental implant according to claim 3, wherein the ceramic coating is a titanium oxide ceramic.

5. The dental implant according to claim 1, wherein the ceramic coating contains at least one of a titanium oxide ceramic and a zirconium oxide ceramic.

6. The dental implant according to claim 1, wherein the thickness of the ceramic coating is 1 nm to 1 mm.

7. The dental implant according to claim 6, wherein at least one of the chemical composition and a physical property of the ceramic coating varies along the thickness of the coating.

8. The dental implant according to claim 1, wherein the ceramic coating has a peak-to-valley height $R_{max}$, according to DIN 4768, of 100 nm to 100 µm.

9. The dental implant according to claim 8, wherein the ceramic coating has a peak-to-valley height $R_{max}$ of 100 nm to 50 µm.

10. The dental implant according to claim 8, wherein the ceramic coating has a peak-to-valley height $R_{max}$ of 100 nm to 5 µm.

11. The dental implant according to claim 1, wherein the thickness of the ceramic coating decreases continuously towards the bone contact surface.

12. The dental implant according to claim 1, wherein the ceramic coating reaches as far as a projection in the transition area from the bone contact surface to the soft tissue contact surface, which projection is compensated by the ceramic coating.

13. The dental implant according to claim 1, wherein an edge of the ceramic coating is formed along the circumference of the implant in a curved shape, with at least one rise and one dip, so that the natural shape of the bone is simulated by the edge.

14. The dental implant according to claim 1, wherein the osseointegration-compatible bone contact surface is roughened, hydroxylated and hydrophilic.

15. The dental implant according to claim 1, wherein the thickness of the ceramic coating is 200 nm to 100 µm.

16. Method of coating a dental implant comprising:
coating the dental implant, the dental implant comprising an integral base body of the dental implant having a bone contact surface, a soft tissue contact surface of the dental implant and a transition area of the dental implant from the bone contact surface to the soft tissue contact surface, wherein the bone contact surface comprises an osseointegration-compatible metal or of an alloy of such a metal, and wherein a ceramic coating comprising at least one of titanium oxide, zirconium oxide and aluminum oxide is applied by anodic oxidation under spark discharge to the soft tissue contact surface and to at least a portion of the transition area adjacent the soft tissue contact surface, and the ceramic coating is not applied to the bone contact surface to preserve the osseointegration-compatible properties of the metal or metal alloy base body.

17. Method according to claim 16, wherein the ceramic coating is a same-type coating comprising an oxide ceramic of the same metal or metal alloy as the oxide ceramic comprising the base body.

18. Method according to claim 16, wherein areas of the implant are at least temporarily covered over so that they are not accessible to the ceramic coating.

19. Method according to claim 16, wherein the surface of the ceramic coating is at least partially roughed by physical and/or chemical processes.

20. The dental implant according to claim 1, wherein the thickness of the ceramic coating effectively avoids the colour of the base body of the dental implant showing through the soft tissue in the implanted state.

21. Method according to claim 16, wherein the base body is made at least partially of titanium or of a titanium alloy.

22. Method according to claim 21, wherein the ceramic coating is a titanium oxide ceramic.

23. Method according to claim 16, wherein the ceramic coating contains at least one of a titanium oxide ceramic and a zirconium oxide ceramic.

24. Method according to claim 16, wherein the thickness of the ceramic coating is 1 nm to 1 mm.

25. Method according to claim 24, wherein at least one of the chemical composition and a physical property of the ceramic coating varies along the thickness of the coating.

26. Method according to claim 16, wherein the ceramic coating has a peak-to-valley height $R_{max}$, according to DIN 4768, of 100 nm to 100 µm.

27. Method according to claim 26, wherein the ceramic coating has a peak-to-valley height $R_{max}$ of 100 nm to 50 µm.

28. Method according to claim 26, wherein the ceramic coating has a peak-to-valley height $R_{max}$ of 100 nm to 5 µm.

29. Method according to claim 16, wherein the thickness of the ceramic coating decreases continuously towards the bone contact surface.

30. Method according to claim 16, wherein the ceramic coating reaches as far as a projection in the transition area from the bone contact surface to the soft tissue contact surface, which projection is compensated by the ceramic coating.

31. Method according to claim 16, wherein an edge of the ceramic coating is formed along the circumference of the implant in a curved shape, with at least one rise and one dip, so that the natural shape of the bone is simulated by the edge.

32. Method according to claim 16, wherein the osseointegration-compatible bone contact surface is roughened, hydroxylated and hydrophilic.

33. Method according to claim 16, wherein the thickness of the ceramic coating is 200 nm to 100 µm.

34. Method according to claim 16, wherein the thickness of the ceramic coating effectively avoids the colour of the base body of the implant showing through the soft tissue in the implanted state.

* * * * *